(12) United States Patent
Brocia

(10) Patent No.: US 7,553,614 B2
(45) Date of Patent: Jun. 30, 2009

(54) HIGH SENSITIVITY FLUOROMETRIC ASSAYS

(76) Inventor: Robert W. Brocia, 15 Moore Rd., Bronxville, NY (US) 10708

( * ) Notice: Subject to any disclaimer, the term of this patent is extended or adjusted under 35 U.S.C. 154(b) by 152 days.

(21) Appl. No.: 10/775,953

(22) Filed: Feb. 9, 2004

(65) Prior Publication Data
US 2005/0042707 A1 Feb. 24, 2005

Related U.S. Application Data

(63) Continuation-in-part of application No. 08/496,806, filed on Jun. 29, 1995, now abandoned.

(51) Int. Cl.
*C12Q 1/00* (2006.01)
(52) U.S. Cl. .............. 435/4; 435/14; 435/69.2
(58) Field of Classification Search ............ 435/4, 435/69.2
See application file for complete search history.

(56) References Cited

U.S. PATENT DOCUMENTS

| 4,277,437 | A | * | 7/1981 | Maggio | 422/61 |
| 4,318,707 | A | * | 3/1982 | Litman et al. | 436/537 |
| 4,798,788 | A | | 1/1989 | Sands | 435/37 |
| 4,853,327 | A | | 8/1989 | Dattagupta | 435/6 |
| 5,173,434 | A | * | 12/1992 | Morris et al. | 436/172 |
| 5,254,477 | A | | 10/1993 | Walt | 436/172 |
| 5,459,567 | A | | 10/1995 | Brocia | 356/318 |
| 5,565,328 | A | | 10/1996 | Bascomb et al. | 435/25 |
| 5,744,320 | A | | 4/1998 | Sherf et al. | 435/8 |
| 2005/0233401 | A1 | * | 10/2005 | Brocia | 435/15 |

FOREIGN PATENT DOCUMENTS

| EP | 0 171 158 | 12/1986 |
| EP | 0 091 837 | 7/1989 |

OTHER PUBLICATIONS

Lakowicz, Joseph Principles of Fluorescence Spectroscopy Plenum Press, NY. 1983, Chapter 9, Quenching of Fluorescence, pp. 257-295.*
Ando et al., Analytical Biochemistry (1983) 129:170-175.
Blumberg et al., Clin. Chem. (1980) 26:409-413.
Carmel et al., Eur. J. Biochemistry (1977) 73:617-625.
Carmel et al., Eur. J. Biochemistry (1978) 87:265-273.
Chen, Analytical Letters (1978) B11(3):249-255.
Fleminger et al., Eur. J. Biochem. (1982) 125:609-615.
Florentin et al., Analytical Biochemistry (1984) 141:62-69.
Haugland, Handbook of Fluorescent Probes and Research Chemicals, 6th ed. by Molecular Probes, Eugene, OR.
Yaron et al., Analytical Biochemistry (1979) 95:228-235.

* cited by examiner

*Primary Examiner*—Ralph Gitomer
(74) *Attorney, Agent, or Firm*—Morrison & Foerster LLP

(57) ABSTRACT

Spectrophotometric assays are rendered more sensitive by adding to the assay mixture a light-emitting moiety. The decrease in intensity of light emitted due to the presence of a light-absorbing moiety associated with the photometric assay is much more sensitive to analyte than the absorbance of the light-absorbing moiety itself.

3 Claims, No Drawings

HIGH SENSITIVITY FLUOROMETRIC ASSAYS

CROSS-REFERENCED RELATED APPLICATIONS

This application is a continuation-in-part of U.S. Ser. No. 08/496,806 filed 29 Jun. 1995, now abandoned, the contents of which are incorporated herein by reference.

TECHNICAL FIELD

The invention is directed to improvements in colorimetric and turbidimetric assays, especially useful in analysis of biological samples.

BACKGROUND

The use of calorimetric and turbidimetric assays for determination of concentration or amount of an analyte in a fluid is well known. Briefly, the analyte is itself able to absorb light or its presence in the sample results in the formation of the compound that absorbs light. Alternatively, the compound itself or its presence in a fluid may result in the formation of turbidity which scatters light, resulting in a diminution in detectable light in a single dimension. Fluorescence assays are also well known; again, the analyte itself may be fluorescent or more commonly its presence in solution results in the formation of a fluorescent moiety; subjecting the fluorescent moiety to a wavelength that it is capable of absorbing results in emission of a somewhat lower wavelength. Typically, in such assays, the detector for the emitted light is orthogonal to the radiation source that effects the emission. The present invention improves the sensitivity of colorimetric and turbidimetric assays by measuring the effect of the generated color or turbidity on the fluorescence of a fluorescent moiety added to the reaction mixture in a configuration typical of fluorescence-based assay.

DISCLOSURE OF THE INVENTION

The invention assays are alternative measurement approaches to colorimetric or turbidimetric assays, in particular with respect to biomedical applications such as blood tests, urinalysis and the like. The invention assays are adaptable to various formats, including, for example, assays for enzyme activity where the enzyme is able to convert a substrate to a colored product, assays for substrates that can themselves be converted to colored products, turbidimetric assays, for example, effected by the reaction of antigens with antibodies, and the like. The practice of these methods in the context of the modifications made by the invention methods results in enhanced sensitivity of the assay, thus permitting smaller quantities of materials to be used. For example, the volume of blood needed to perform blood tests is diminished.

Thus, in one aspect, the invention is directed to a method to determine the concentration of analyte in a sample which method comprises providing a reaction mixture containing said sample, a light emitting moiety, and if needed, reagent(s) that generate a light absorbing moiety in proportion to the concentration of analyte; and determining the decrease in light emitted from said light emitter as a function of concentration of analyte.

In another aspect, the invention is directed to an improved method to determine the concentration of analyte in a fluid in a colorimetric or turbidimetric assay, wherein the improvement comprises measuring the diminution of fluorescence of a light emitting moiety added to the colorimetric or turbidimetric assay mixture.

MODES OF CARRYING OUT THE INVENTION

The assays of the invention employ reaction mixtures with two indicators for the assessment of analyte. The first indicator is the colored or insoluble product which results from the presence of analyte, the intensity of the color and the turbidity of the reaction mixture being proportional to the amount or concentration of analyte present. Auxiliary reagents may be required in order to generate these first indicators. For example, in an analysis for hydrogen peroxide, a peroxidase is required to generate a colored product. In an assay for glucose, an additional reagents are also required to generate color. Assays for enzyme activity such as esterase activity require the addition of substrate in order to generate a colored product. Thus, the first indicator present in the reaction mixture is the color or precipitate causing turbidity that is generated by the presence of analyte.

A second indicator is also present in the reaction mixture. The second indicator is a light emitting source that is phosphorescent, fluorescent or luminescent, preferably fluorescent. Typical second indicators include, for example, fluorescein, calcein, and NBD.

In a typical assay, the reaction mixture contains the sample to be tested for analyte, optionally reagents which convert the analyte to the first indicator or effect conversion of a substrate to first indicator in proportion to the amount or concentration of analyte; and a second indicator which will emit light and wherein the light emitted by the second indicator will be dampened or diminished by the presence of the first indicator.

A number of mechanisms are possible whereby this can occur. The light emitted by the second indicator may simply be absorbed by the first indicator or there may be a physical interaction between the first and second indicator such that the emission of fluorescence is inhibited. Alternatively, if the first indicator makes the reaction mixture turbid, simple interruption of the light path may be the mechanism.

In a typical arrangement using a fluorescent second indicator, the reaction mixture is subjected to a beam of light comprising the wavelength absorbed by the second indicator. A detector is placed at an angle, preferably 90 degrees, to the incoming beam to detect any fluorescent light emitted. It has been found that the decrease in light detectable is directly proportional to the concentration of the first indicator, and thus proportional to the concentration of the analyte.

The increased sensitivity of the invention assay is apparent from the following comparison of analysis determining concentration using a standard calorimetric assay of Lowry with the analysis method of the invention. Table 1 shows the results of the standard calorimetric Lowry method where the absorption of color generated is measured spectrophotometrically. As apparent, the sensitivity of the assay is in the microgram range.

TABLE 1

| Protein Micrograms | Absorbence (Optical) Density, O.D.) |
|---|---|
| 0 | 0.109 |
| 25 | 0.4575 |
| 50 | 0.769 |

Table 2 shows the results obtained by adding, to the Lowry reaction mixtures, the second indicator, in this case the fluorescent compound NBD. Because the assay is more sensitive, the level of protein provided to the containers is 1,000 fold less than that shown in Table 1.

TABLE 2

| Protein Micrograms | Fluorescence Intensity |
|---|---|
| 0 | 1496 |
| 0.025 | 1429 |
| 0.05 | 1361 |

As seen, the decrease in fluorescence intensity is linear with regard to concentration.

Prior to the addition of the second indicator, the color generated at the levels of protein shown in Table 2 is undetectable to the naked eye. However, when the second indicator was added a decrease in fluorescence was visible in the vessels that contained protein.

In an additional comparison, a glucose test kit supplied by Sigma Chemical Company, St. Louis, Mo. was used to assay glucose. The reagents to convert glucose to the first indicator are glucose oxidase, peroxidase, and O-dianisidine. The glucose oxidase converts glucose to gluconic acid and hydrogen peroxide which is decomposed by peroxidase to oxidize O-dianisidine; oxidized O-dianisidine is yellow. When used at concentrations in the range of 0.1-0.125 mg/dl, no yellow color is visible. However, when the second indicator NBD is added to the reaction mixture, a decrease in fluorescence intensity, linear with respect to glucose concentration is obtained with the addressing of glucose as shown in Table 3.

TABLE 3

| Glucose (mg/dl) | Fluorescence Intensity |
|---|---|
| 0.1 | 2223.5 |
| 0.111 | 2179 |
| 0.125 | 2105 |

The concentration of glucose detected by the invention method is thus 1,000 fold less than indicated for the Sigma kit protocol.

Because of the higher sensitivity of the assay method of the present invention, standard blood tests ordinarily performed on ml quantities of blood or plasma, where the blood or plasma is abstracted with a syringe can instead be performed on µl quantities obtained using a finger prick.

In summary, standard photometric assays, which may be colorimetric or turbidimetric, where the first indicator is the colored or turbid substance, whose absorbance is proportional to concentration of analyte, can be improved by adding a second indicator, which is a fluorescence-emitting moiety and using the diminution of the level of fluorescence as the measure of analyte concentration, rather than the absorbance of the color or turbidity which are considered first indicators. The method can be performed by adapting auto-analyzers that currently utilize the absorbance or transmittance methods of measuring color density or turbidity in photometric assays to determine analyte levels by including a fluorescence reader on such instruments. The result is a multifold increase in measurement sensitivity.

Current blood testing methods require blood samples in the amount of 5-15 ml to obtain results in a battery of blood tests; this can be reduced to the range of 2-15 µl for the same battery of tests when the tests are modified according to the method of the invention.

The first indicator may be the analyte itself, for example, in the case of measurement of red blood cell concentration in diluted blood. Alternatively, the analyte may be converted into a colored substance, such as the conversion of hydrogen peroxide into a colored material by treatment with peroxidase, an oxidizing agent, and a complexing agent. In still another alternative, the analyte may inherently possess turbidity, such as a cell suspension, or turbidity may be produced by reaction with the analyte, as in the formation of antigen-antibody complexes.

In still another alternative, the analyte may be, for example, an enzyme which converts a colorless substrate into a colored one. In this case, the analyte is not itself converted into the first indicator, but the concentration of first indicator is proportional to the concentration of analyte. In any case, the first indicator is a colored moiety or a turbid moiety whose concentration is proportional to analyte. The improvement of the present invention is to include in the assay mixture a second indicator which is a light-emitting moiety, where the intensity of light emission is decreased proportional to the concentration of first indicator.

The invention claimed is:

1. A method to determine the concentration of an analyte in a sample which method comprises
   providing a reaction mixture containing said sample, a fluorophore, and reagent(s) to generate an indicator in proportion to the concentration of analyte which indicator can physically interact with the fluorophore to prevent light emission from any molecules of fluorophore that physically interact with the indicator in the reaction mixture; and
   determining any decrease in light emitted from said reaction mixture as compared to a control reaction mixture that lacks said sample as a measure of concentration of analyte in the sample, and
   wherein the analyte is a substrate for an enzyme and the indicator is a product of action on said substrate by the enzyme.

2. The method of claim 1 wherein the indicator is hydrogen peroxide.

3. The method of claim 1 wherein the enzyme includes glucose oxidase and the substrate is glucose.

* * * * *